United States Patent
Brandeis (10) Patent No.: US 9,913,633 B2
(45) Date of Patent: Mar. 13, 2018

(54) ABLATION CATHETER FOR BLOOD VESSEL ABLATION AND METHODS OF USING THEREOF

(71) Applicant: V.V.T. Med Ltd., Kfar-Saba (IL)

(72) Inventor: Zeev Brandeis, Rosh HaAyin (IL)

(73) Assignee: V.V.T. Med Ltd., Kfar-Saba (IL)

(*) Notice: Subject to any disclaimer, the term of this patent is extended or adjusted under 35 U.S.C. 154(b) by 319 days.

(21) Appl. No.: 14/418,084

(22) PCT Filed: Jul. 16, 2013

(86) PCT No.: PCT/IL2013/050602
§ 371 (c)(1),
(2) Date: Jan. 29, 2015

(87) PCT Pub. No.: WO2014/020590
PCT Pub. Date: Feb. 6, 2014

(65) Prior Publication Data
US 2015/0157303 A1    Jun. 11, 2015

Related U.S. Application Data

(60) Provisional application No. 61/676,963, filed on Jul. 29, 2012.

(51) Int. Cl.
*A61B 17/3207* (2006.01)
*A61B 17/00* (2006.01)
(Continued)

(52) U.S. Cl.
CPC .... *A61B 17/00008* (2013.01); *A61B 17/3207* (2013.01); *A61B 17/320725* (2013.01);
(Continued)

(58) Field of Classification Search
CPC .......... A61B 17/00008; A61B 17/3207; A61B 17/320725; A61B 2017/00778;
(Continued)

(56) References Cited

U.S. PATENT DOCUMENTS

| 4,650,466 A | 3/1987 | Luther |
| 4,921,484 A | 5/1990 | Hillstead |

(Continued)

FOREIGN PATENT DOCUMENTS

| WO | WO 2005/112813 | 12/2005 |
| WO | WO 01/74255 | 10/2011 |
| WO | WO 2014/020590 | 2/2014 |

OTHER PUBLICATIONS

International Search Report and the Written Opinion dated Nov. 3, 2013 From the International Searching Authority Re. Application No. PCT/IL2013/050602.

(Continued)

*Primary Examiner* — Bhisma Mehta
*Assistant Examiner* — James D Ponton (57) ABSTRACT

An ablation catheter system is disclosed that comprises a channel and a tubular braided element having an outer circumferential surface and a lumen. The tubular braided element is sized and shaped to be placed in the channel when in a compressed configuration and to be expanded in a target area of a blood vessel in a manner that the outer circumferential surface touches the walls of the target blood vessel in the target area when in an expanded configuration. The system also includes a longitudinal maneuvering element which is mechanically connected to a distal end of the tubular braided element and set to pull the distal end into the lumen so as to curve radially and outwardly a plurality of annular segments of the expand tubular braided element in a sequential manner.

15 Claims, 6 Drawing Sheets

(51) Int. Cl.
*A61M 25/10* (2013.01)
*A61B 17/32* (2006.01)

(52) U.S. Cl.
CPC .............. *A61B 2017/00778* (2013.01); *A61B 2017/320004* (2013.01); *A61B 2017/320008* (2013.01); *A61B 2017/320741* (2013.01); *A61M 2025/105* (2013.01); *A61M 2025/1086* (2013.01)

(58) Field of Classification Search
CPC ....... A61B 2017/320004; A61B 2017/320008; A61B 2017/320012; A61B 2017/320741; A61B 17/221; A61B 2017/2212; A61B 2017/2215; A61M 25/0119; A61M 2025/109; A61M 2025/1004; A61M 2025/1047; A61M 2025/105; A61M 2025/1086; A61M 25/1002
USPC ........................................................ 604/271
See application file for complete search history.

(56) References Cited

U.S. PATENT DOCUMENTS

| | | | |
|---|---|---|---|
| 5,653,684 A | 8/1997 | Laptewicz et al. | |
| 5,792,157 A * | 8/1998 | Mische | A61B 17/320725 606/159 |
| 6,096,054 A | 8/2000 | Wyzgala et al. | |
| 7,722,604 B2 | 5/2010 | Brown, III et al. | |
| 2003/0097114 A1 | 5/2003 | Ouriel et al. | |
| 2004/0181237 A1* | 9/2004 | Forde | A61B 17/12122 606/108 |
| 2005/0085880 A1 | 4/2005 | Truckai et al. | |
| 2008/0262337 A1* | 10/2008 | Falwell | A61B 18/1492 600/374 |

OTHER PUBLICATIONS

Communication Pursuant to Article 94(3) EPC dated Jan. 13, 2017 From the European Patent Office Re. Application No. 13826243.1. (5 Pages).
Supplementary European Search Report and the European Search Opinion dated Feb. 24, 2016 From the European Patent Office Re. Application No. 13826243.1.
International Preliminary Report on Patentability dated Feb. 12, 2015 From the International Bureau of WIPO Re. Application No. PCT/IL2013/050602.
Summons to Attend Oral Proceedings Pursuant to Rule 115(1) EPC dated Sep. 1, 2017 From the European Patent Office Re. Application No. 13826243.1. (4 Pages).

* cited by examiner

ABLATION CATHETER FOR BLOOD VESSEL ABLATION AND METHODS OF USING THEREOF

RELATED APPLICATIONS

This application is a National Phase of PCT Patent Application No. PCT/IL2013/050602having International filing date of Jul. 16, 2013, which claims the benefit of priority under 35 USC § 119(e) of U.S. Provisional Patent Application No. 61/676,963filed on Jul. 29, 2012. The contents of the above applications are all incorporated by reference as if fully set forth herein in their entirety.

FIELD AND BACKGROUND OF THE INVENTION

The present invention, in some embodiments thereof, relates to a braided element for blood vessel ablation and to methods of using thereof and, more particularly, but not exclusively, to an ablation catheter system for use in minimally invasive phlebectomy procedures.

All catheter methods are invasive. All catheter methods cause trauma to blood vessels that they are directed through. Even for catheter procedures where some level of trauma is desired, such as vein ablation, exceeding a desired level of trauma to the blood vessel can cause undesirable complication to the surrounding living tissues. For example, the common practice invasive phlebectomy procedure is a mechanical method for removing a vein by insertion a wire into the vein and rotating the wire therein. The rotation of the wire irritates the vein sufficiently to create hematoma, collapse of the vein, and allow eventual dissolution of the vein remnant into the body. Other catheter treatment methods of vein ablation or blood vessel ablation likewise risk causing undesirable levels of trauma to the blood vessel, and often also risk secondary trauma to the surrounding living tissues.

SUMMARY OF THE INVENTION

According to an aspect of some embodiments of the present invention there is provided an ablation catheter system for blood vessel ablation and methods of using thereof. Embodiments of an ablation catheter method, properly performed, allow for control of the degree of primary trauma to the blood vessel and for reduced secondary trauma to the surrounding tissues. Secondary trauma is controlled essentially because the tubular braided element of the ablation catheter system may be used to apply minimum necessary procedural wounding pressure to the wall of a blood vessel.

In use, a tubular braided element of the catheter system is expanded along the contour of the blood vessel wall, following the topography of the blood vessel. Just as the width of the blood vessel lumen may vary along the blood vessel's length, likewise the tubular braided element diameter may be adapted accordingly. Then, the distal end of the tubular braided element is rolled into its longitudinal lumen. Retracting the tubular braided element back from its expanding position along the blood vessel wall applies a relatively mild wounding force on the blood vessel wall, which may be a vein with sensitive walls. The infolded braided tubular element segment has an elasticity coefficient that is reduced in relation to the elasticity coefficient of the tubular braided element in the expand position. Moreover, the infolded segment is at least slightly pushed towards the blood vessel wall in relation to the position of the tubular braided element in a expand position. The retracting of the tubular braided element scratches the blood vessel along the longitudinal path of the tubular braided element. As the tubular braided element distal end is adapted to the contour and variable width of the blood vessel, the applied wounding force remains substantially uniform along the blood vessel even though the blood vessel has changing counter and width.

According to some embodiments of the present invention, there is provided an ablation catheter system. The system comprises a channel, a tubular braided element having an outer circumferential surface and a lumen, the tubular braided element being sized and shaped to be placed in the channel when in a compressed configuration and to be expand in a target area of a blood vessel in a manner that the outer circumferential surface touches the walls of the target blood vessel in the target area when in a expand configuration, and a longitudinal maneuvering element which is mechanically connected to a distal end of the tubular braided element and set to pull the distal end into the lumen so as to curve radially and outwardly a plurality of annular segments of the expand tubular braided element in a sequential manner.

Optionally, the channel is an inner channel which is placed in and along a catheter, the inner channel allows placing the tubular braided element in place while retracting the inner channel, facilitating the tubular braided element to expand from the compressed configuration to a expand configuration.

Optionally, the blood vessel is a vein.

Optionally, the tubular braided element comprises a mesh having a plurality of parallel fibers each with a different rigidity coefficient.

Optionally, at least the outer circumferential surface is coated with a drug.

Optionally, the system further includes a fluid channel located within the channel and set to conduct fluid along the channel, between the target area and an extrabody container.

More optionally, the fluid channel having a fluid releasing head at its tip, the fluid releasing head having at least one aperture directed to release fluid toward the walls or to withdraw fluid from the target area.

Optionally, the tubular braided element is made from a fiber made of a material selected from a group consisting of: metallic fiber, organic fiber, glass fiber, bio-reactive fiber, catalytic fiber, bio-soluble fiber, inert fiber, highly flexible fiber, abrasive fiber, single filament fiber, and a combination of the aforesaid.

According to some embodiments of the present invention, there is a method for treating a blood vessel. The method comprises conducting a tubular braided element having an outer circumferential surface and a lumen in a compressed configuration using a catheter channel to a target area in a blood vessel, extracting at least a portion of the tubular braided element from the channel so as to expand the portion in a manner that the outer circumferential surface applies a first pressure on walls of the target blood vessel, and pulling a distal end of the expand tubular braided element into the lumen so as to curve radially and outwardly a plurality of annular segments of the expand tubular braided element in a sequential manner. Each the annular segment applies a second pressure on the target blood vessel when being curved than the first pressure.

Optionally, the pulling comprises wounding the walls of the target blood vessel during the pulling.

Optionally, the annular segment is curved in a poloidal direction.

Optionally, the method further comprises conducting a drug along the channel and releasing the drug during the pulling.

Optionally, the extracting is performed by maintaining the orientation of the tubular braided element along the target area while retracting the channel.

Optionally, the method further comprises pulling the tubular braided element in the channel further after the distal end exceeds the lumen in a proximal direction, pushing the tubular braided element to bring the distal end to a proximity with a tip of the channel, conducting the tubular braided element to another target area in the blood vessel, and repeating the conducting, the extracting and the pulling.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to a method for treatment of a blood vessel and to a system for use therewith and, more particularly, but not exclusively, to a catheter based method for use in invasive procedures for ablation of a blood vessel, for example removal of the varicose veins, ablation of spider veins and of similar blood vessels, and/or the like.

Embodiments of a present invention have a tubular braided element for insertion into a blood vessel and extraction from the blood vessel. Ablation procedures, using a tubular braided element of appropriate materials and of appropriate tensile strength, allow control of primary trauma and secondary trauma to sensitive blood vessels. Accordingly, the tubular braided element requires coordinated appurtenances to facilitate controlled insertion, ablation, and extraction. Hereinafter are described aspects of properties of a tubular braided element, embodiments of an ablation catheter system incorporating the tubular braided element with requisite and optional appurtenances, and methods for using these systems to accomplish blood vessel ablation.

According to some embodiments of the present invention, there are provided methods and systems wherein a tubular braided element is used during catheterization for blood vessel ablation. As used herein, the term "braid" in the context of the instant invention, relates to a thread-like or ribbon-like construction that appears as a woven or extruded mesh, a network, a grid, a net, a cross linked multi-helix, a trellis-like structure and/or the like.

According to some embodiments of the present invention, there are provided ablation systems and methods where a channel is conducted in a blood vessel to extract and expand a braided tubular element in a target segment of the blood vessel. When pulling a distal portion of the braided tubular element into the lumen of the braided tubular element while a proximal portion thereof remains in place, a wounding pressure is applied on the inner blood vessel walls. This wounding pressure is sufficient to trigger the ablation of the blood vessel without damaging surrounding tissues.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
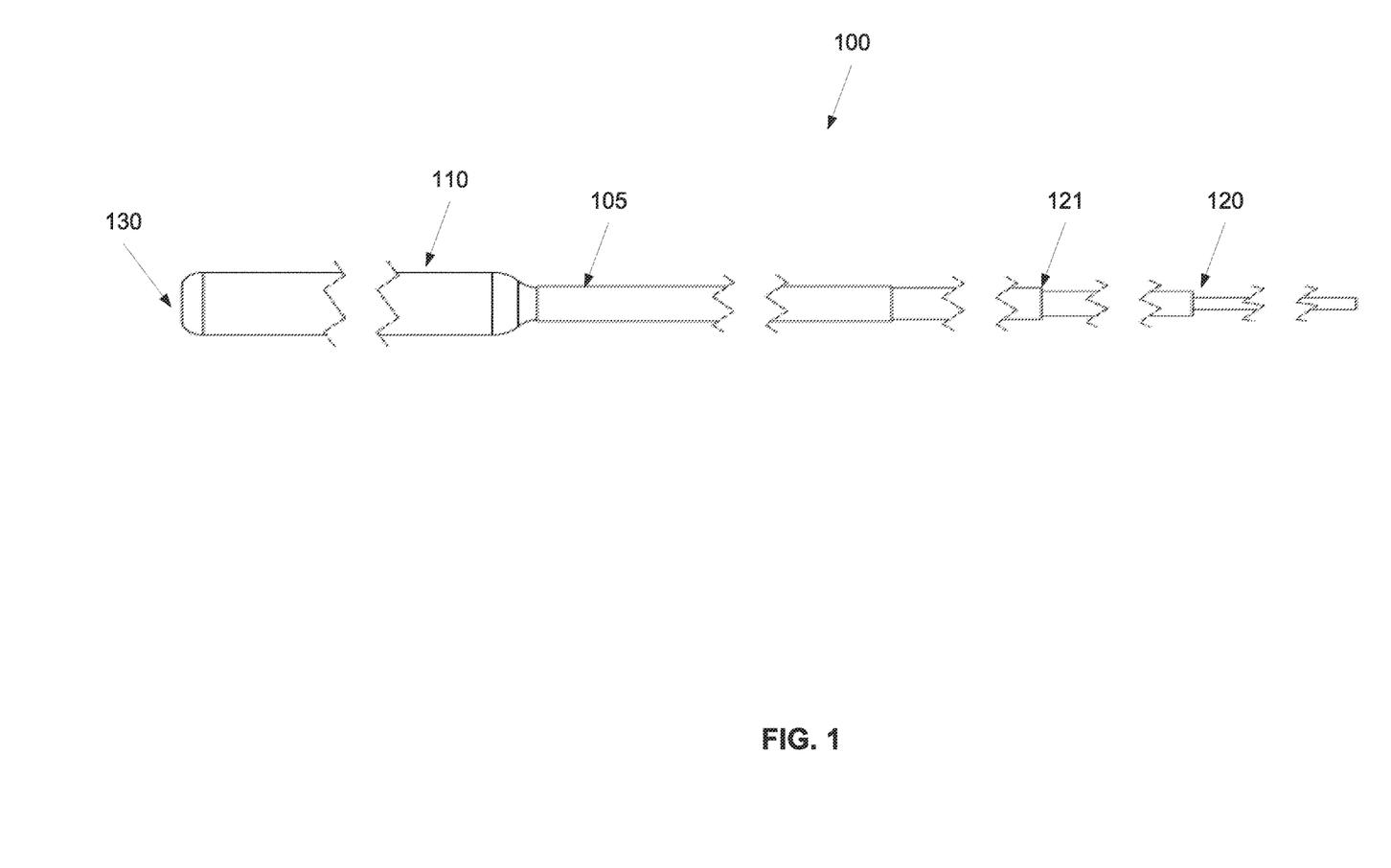
FIG. 1 is a schematic illustration depicting an exemplary ablation catheter system having a tubular braided element, according to some embodiments of the present invention.

Reference is now made to FIG. 1, which is a schematic illustration depicting an exemplary ablation catheter system 100 having a tubular braided element 110 and a catheter channel 105 for conducting the tubular braided element 110, according to some embodiments of the present invention. In use, a distal end of the catheter channel 105 stores an inner channel 121 that confines the tubular braided element 110 in a compressed configuration such that the tubular braided element 110 may slide longitudinally out from the distal end of the catheter channel 105 and the inner channel 121, for example when a longitudinal pulling element 120 that is attached to distal end of the tubular braided element 110 remains in place while the catheter channel 105 and the inner channel 121 are retracted. The longitudinal pulling element 120 may be, for example, a flexible rod or a wire. The inner channel 121 is mounted along and in a longitudinal axis space of the catheter channel 105. The longitudinal pulling element 120 is optionally connected to the distal end (or tip) of the tubular braided element 110 and the inner walls of the inner channel 121 are optionally connected to the proximal end of the tubular braided element 110, see also 355 in FIGS. 4 and 5. The tip of the tubular braided element 110 is marked and referred to as tip 130. As will be explained with reference to FIG. 2, the distal end of the tubular braided element 110 may be extracted within the lumen of the tubular braided element by pulling the tubular braided element 110 in the proximal direction.

Those skilled in the art of blood vessel ablation recognize the complexity of blood vessels in need of ablation. These typically include complex pathway configurations, inconsistent blood vessel wall flexibility, strength, surface sensitivity, and the like. Accordingly, uses of embodiments of the instant invention provide those skilled in these arts with a capability to manage aspects of the hematoma trauma being induced during the ablation and for respective segments of the blood vessel.

As used herein, catheter channel 105 means any one or more conduits capable of supporting and guiding the tubular braided element 110 into a blood vessel.

As used herein, longitudinal pulling element in the context of the instant invention relates to narrow length of tensile material capable of attachment to an end of a tubular braided element. Furthermore, the flexibility coefficients of the inner channel 121 and the longitudinal pulling element 120 allows accompanying the tubular braided element 110 into and out of a predetermined blood vessel. The longitudinal pulling element 120 has a sufficient tensile strength to facilitate a full or partial roll back (described in detail in FIG. 2) of the attached tubular braided element 110 into its lumen.

In use, tubular braided element 110 is pulled by the longitudinal pulling element 120 that is mechanically connected to a distal end thereof into the lumen of the tubular braided element 110. This is optionally done while the inner channel 121 is maintained in place, in touch with the proximal end. In such a manner, a plurality of annular segments of the expanded tubular braided element are radially curved and outwardly in a sequential manner. This applies a wounding pressure on the inner blood vessel wall. The wounding pressure induces ablation.

All of the above terms relate to biocompatible components and/or appurtenances which are of materials of appropriate surgical biocompatibility and capable of appropriate degree of sterility and/or sterilization.

According to embodiments of the present invention, specific properties of a tubular braided element 110 are used for ablation of blood vessels, such as veins. For example, reference is now made to FIG. 2, which is an exploded view of an annulus-wise inversion of a tubular braided element 200, according to some embodiments of the present invention. Here, the tubular braided element 200 is shown, in isolation from the instant system and the instant method, in order to illustrate functional aspects which are relevant when utilized in a blood vessel ablation. The tubular braided element 200 is external and a respectively internal longitudinal pulling element 205 that is attached to the tubular braided element 200 at their mutual distal ends 210.

Figure 2:
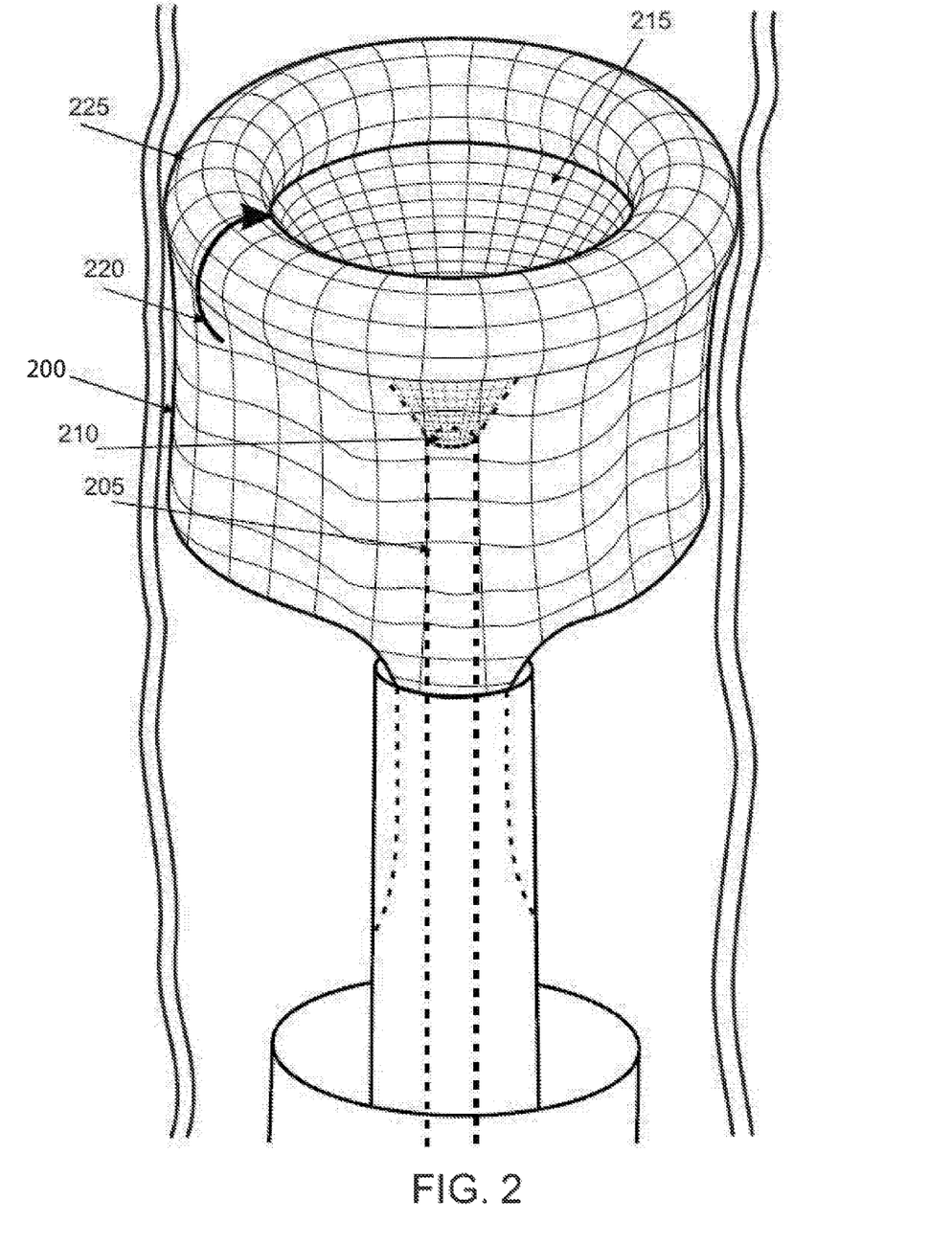
FIG. 2 is an exploded view of an annulus-wise inversion of a tubular braided element, according to some embodiments of the present invention.

Another property of a tubular braided element 200 is that a distal end 210 of the tubular braided element 200 may be rolled up back into the lumen 215 of the tubular braided element 200. In use annular, segments of the tubular braided element 200, which are optionally continuous segments which are not physically separated from one another, are sequentially curved radially and outwardly to apply friction pressure for light scratching on the blood vessel walls. The pressure wounds the blood vessel to induce ablation. As the tubular braided element 200 may be expanded to fit the curvature of the blood vessel, the curving also follows the curvature of the blood vessel.

In the general context of geometric topology the movement of the distal tip of the tubular braided element 200 may be referred to as a poloidal direction 220, which is the short way around an imaginary torus 225 (which is a reference shape that is sometimes called an annulus, a ring, or a doughnut).

An aspect of some embodiments of the instant invention relates to properties of a tubular braided element, particularly to annulus-wise inversion properties of the tubular braided element at the tip region. Various appurtenances are described, and therewith reference is now made to FIGS. 3 and 4, which are a two dimensional (2D) and 3D schematic illustrations depicting an exemplary ablation catheter system, according to some embodiments of the present invention.

Figure 3:
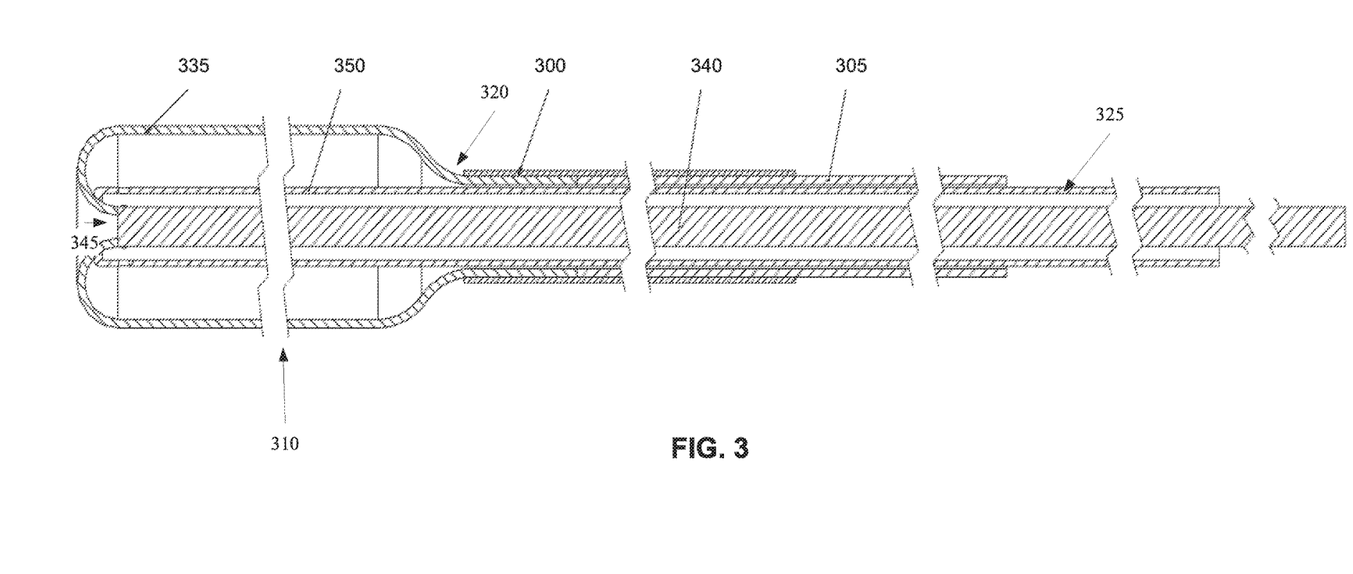
FIG. 3 is a schematic illustration depicting another exemplary ablation catheter system having a tubular braided element, according to some embodiments of the present invention.
Figure 4:
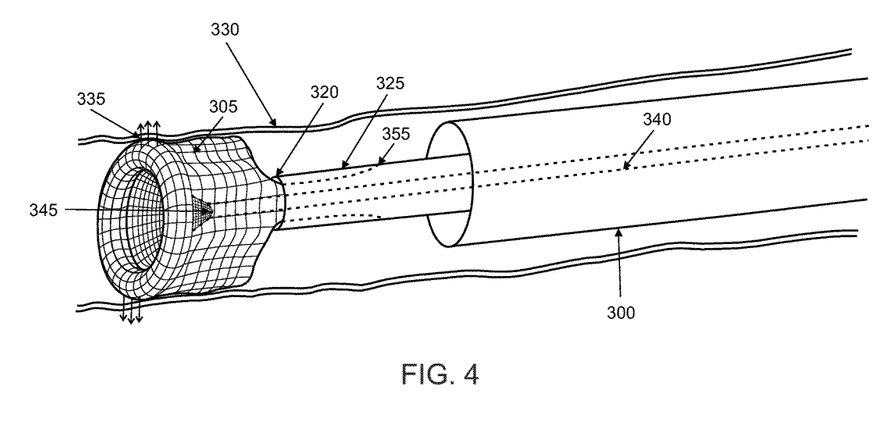
FIG. 4 is a three dimensional (3D) schematic illustration depicting the ablation catheter system of FIG. 3, according to some embodiments of the present invention.

In FIG. 3, the proximal portion of the tubular braided element 305 is bounded between a catheter channel 300 and an inner channel 325. The distal portion 335 of the tubular braided element 305 is expanded. As shown at 345, the tip of a longitudinal pulling element 340 is connected to the distal portion of the tubular braided element 305. A tip portion 350 of the inner channel 325 protrudes from a distal end 320 of the catheter channel 300. Alternatively, as depicted in FIG. 4, the proximal portion of the tubular braided element 305 is attached to the inner walls of the inner channel 325.

In use, a distal portion of the expanded tubular braided element 305 is further expended to apply pressure on the vein walls 330 when the longitudinal pulling element 340 is pulled, optionally while the inner channel 325 remains in place. In such a manner, when the tip of the tubular braided element 305 is expanded, the expanded portion of the distal portion 305 rubs the interior surface of the walls of a surrounding blood vessel 330. The nature of the trauma that is caused to the blood vessel wall may be controlled by adjusting the velocity of retracting the tip of the tubular braided element 305 into the lumen of the tubular braided element 305 or selecting a tubular braided element 305 with a suitable rigidity and/or braided pattern.

It should be noted that after all the tubular braided element 305 is retracted into the inner channel 325, the tubular braided element 305 may be aligned again by pushing the inner channel 325 forward while maintaining the longitudinal pulling element 340 in place, covering the tubular braided element 305 with the channel lumen while leaving a space thereinfront and then pushing the longitudinal pulling element 340 while maintaining the inner channel 325 in place, placing the tubular braided element 305 in the front space. The ability to align the tubular braided element 305 allows sequentially repeating the wounding process, for example the process depicted in FIG. 6 in a plurality of sequential iterations.

Optionally, the tubular braided element 305 is coated with a drug, such as thrombotic and/or sclerotic agent, inducing desired vessel inner wall damage and ablation.

Figure 5:
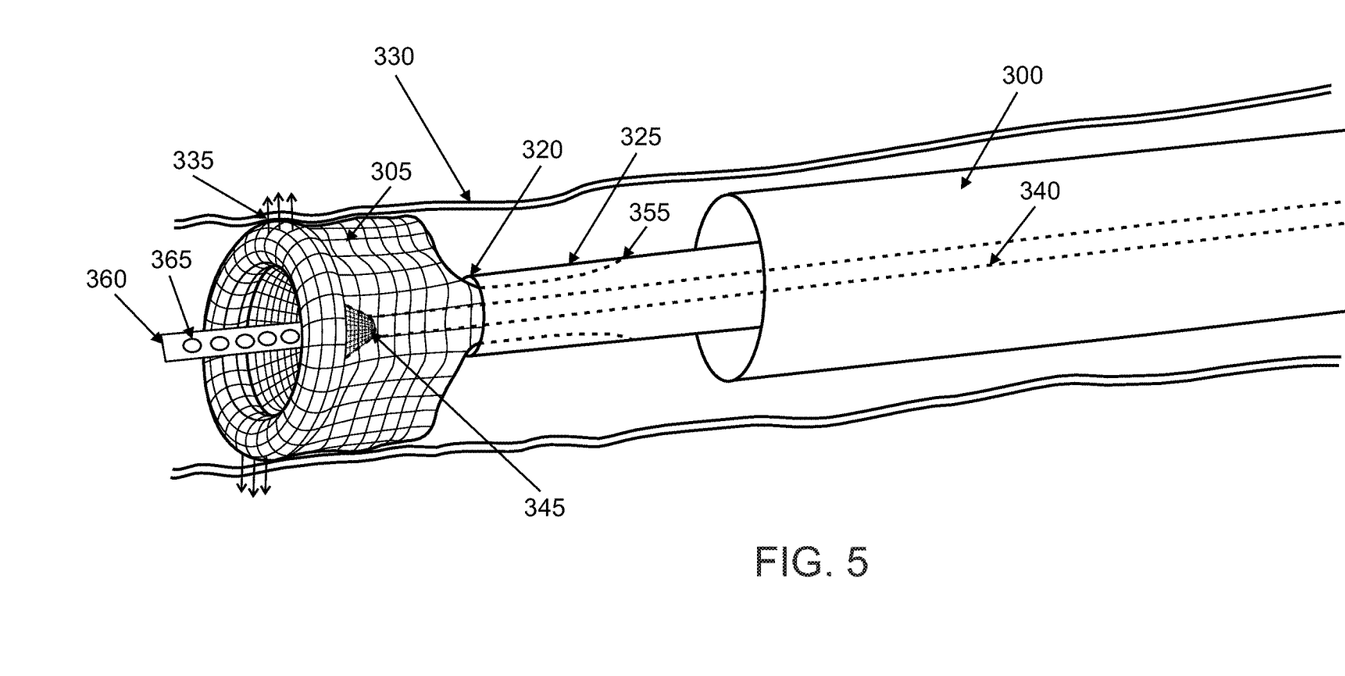
FIG. 5 is a 3D schematic illustration depicting the ablation catheter system of FIG. 3 with an additional fluid channel, according to some embodiments of the present invention.

Optionally, as shown at FIG. 5, the ablation catheter system further includes a fluid channel 360 for releasing a drug or any other fluid, optionally onto the surrounding blood vessel, in conjunction with the wounding of the inner blood vessel wall. Optionally, the drug channel 360 is coaxially located between the longitudinal pulling element 340 and the tubular braided element 305 and/or in the longitudinal pulling element 340. The fluid channel 360 is optionally integrated in or provided in attachment to the longitudinal pulling element 340. Optionally, the channel tip includes a plurality of lateral apertures, such as 365, for releasing the drug onto the blood vessel walls while wounding the blood vessel wall. Various classes of drugs may be released, for example anesthetic, antibiotic, anti-coagulant, thrombotic agents, sclera agents, spasm agents, cell specific, membrane specific targeting drugs, and the like.

Additionally or alternatively, the ablation catheter system further includes a simultaneous fluid extraction and/or aspiration channel for drawing debris and/or blood from the blood vessel, in conjunction with the wounding of the inner blood vessel wall. The fluid extraction channel is optionally integrated in or provided in attachment to the longitudinal pulling element 340. Optionally, the fluid extraction channel tip includes a plurality of lateral apertures for drawing debris that is released from the blood vessel walls while the wounding process is implemented.

According to some embodiments of the present invention, there are provided methods and systems of coordinating with known catheter functions. For example, there are well known catheter procedures which call for injecting fluid into a blood vessel, whereas there are instances where the efficacy of this procedure improves with the stimulus of the blood vessel wall while pulling the tubular braided element 305 across the interior lumen surface of the blood vessel. Thus, according to some embodiments of the method present invention, there are provided, with the inserting of the ablation catheter, a step of injecting a fluid into the blood vessel; and the injecting may be during an inserting of the ablation catheter into the blood vessel, or thereafter.

Optionally, the fluid, for example the drug, is introduced into the blood vessel through the distal end of the channel that is used for conducting the tubular braided element 305. Optionally, subsequent to the injection of fluid or independent of the injection of fluid, suction of fluid may be accomplished via this catheter. Other embodiment examples of coordinating known catheter functions with instant invention methods and systems include activating the longitudinal pulling element 340 of the ablation catheter while the tubular braided element 305 is within the blood vessel.

It should be noted that as the tubular braided element 305 expanding depends on the diameter of the blood lumen, the wounding pressure that is applied by the tubular braided element 305 during the retraction thereof is distributed relatively evenly. As the curvature of the tubular braided element 305 in a expand configuration is determined according to the actual curvature of the blood vessel, no or less excessive pressure is applied on the blood vessel. In such a manner, the pressure applied by this procedure remains within intended primary and/or secondary trauma threshold values to the blood vessel and to the surrounding tissues.

Optionally, the catheter channel 300 includes a sharp distal perforation tip for penetrating into a blood vessel. Alternately, incision, perforation, or equivalent access into an intended portion of the blood vessel may be accomplished independently, and immediately thereafter, the distal portion of the ablation catheter tubular braided element 305 is inserted into the blood vessel, as described below. Optionally, the catheter channel 300 includes flexible portions; so that it is simpler to navigate the tubular braided element 305 a designated portion of an intended blood vessel.

Prior to initial use as a catheter, the tubular braided element 305, the inner channel 325 and longitudinal pulling element 340 are enclosed within the catheter channel 300. Longitudinal motion of the tubular braided element 305 and the longitudinal pulling element 340 in the distal direction are accomplished by pushing the proximal end of the longitudinal pulling element 340 toward the distal end of the inner channel 325 and the catheter channel 300. Pulling the longitudinal pulling element 340 slower than pulling the inner channel 325 extracts the tubular braided element 305 from the catheter channel 300 and allows expanding the tubular braided element 305 in the blood vessel.

After the procedure ends, longitudinal pulling element 340 is retracted together with the tubular braided element 305 at least into the catheter channel 300. Then, the catheter channel 300 is retracted from the blood vessel.

The tubular braided element 305 may include a mesh made of fibers of one or more types, for example metallic, organic, glass, bio-reactive, catalytic, bio-soluble, inert, highly flexible, abrasive, and/or single filament fibers. These fibers have respectively different properties (reactive, adsorptive, absorptive, catalytic, etc.) within the blood vessel and different mechanical properties during the insertion of the catheter 305 into the blood vessel and the extraction of the tubular braided element 305 from the blood vessel.

Optionally, the longitudinal pulling element 340 includes one or more optical fibers which according to some embodiments allow transmittal of laser energy to the distal end of the tubular braided element 305, and according other embodiments allow receiving optical measurements from the distal end of the tubular braided element 305.

Other options for embodiments of the system include aspects when inserting the ablation catheter into the blood vessel further includes determining an appropriate tubular braided element 305 diameter for the blood vessel in accordance with topology metrics of the blood vessel (length of the blood vessel, diameter of the blood vessel, rigidity of the blood vessel, penetrability & fragility of walls of the blood vessel, convolution shape of the axial aspects of the blood vessel, etc.) and in accordance with the treatment of the blood vessel that is being performed. Examples of treatments of a blood vessel that utilize the instant system are invasive phlebectomy, invasive sclerotherapy, and ablating a blood vessel.

Figure 6:
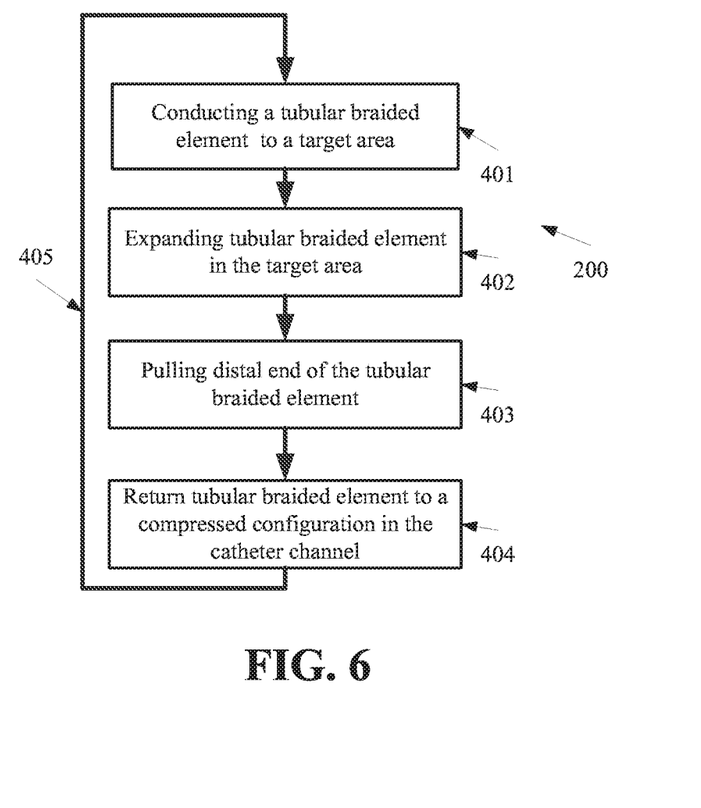
FIG. 6 is a flowchart of an exemplary method for treatment of a blood vessel with an ablation catheter system, according to some embodiments of the present invention.

Reference is now made to FIG. 6, which is a flowchart of an exemplary method for treatment of a blood vessel with a tubular braided element, such as the described above, according to some embodiments of the present invention. First, as shown at 401, the tubular braided element is conducted in a compressed configuration in the lumen of a catheter channel to a target area in a blood vessel. The catheter channel is conducted to an intravascular area of a target blood vessel (guided and slide through the access entry) so that the tubular braided element portion that is substantially within the catheter channel is placed along the length of the blood vessel (is conducted into a target blood vessel).

Now, as shown at 402, at least a portion of the tubular braided element is extracted from the catheter channel and optionally from an inner channel thereof so as to expand the portion in a manner that the outer circumferential surface of the tubular braided element applies a first pressure on walls of the target blood vessel. Optionally, the catheter channel and optionally from an inner channel thereof are retracted while leaving the tubular braided element expand along the blood vessel so that the tubular braided element applies pressure on an inner blood vessel wall of the target blood vessel. Optionally, as described above, a drug may be released while the braided head element is expanded.

Now, as shown at 403, the distal end of the expanded tubular braided element is pulled into the lumen of the tubular braided element so as to curve radially and outwardly a plurality of annular segments of the expanded tubular braided element in a sequential manner. When curved, each annular segment applies a pressure on the target blood vessel. The pressure is higher than the pressure applied by the uncurved tubular braided element in a expand configuration. Optionally, the tubular braided element movement brings a distal portion of the tubular braided element into a lumen of the tubular braided element while a proximal portion of the tubular braided element remains in place.

Now, as shown at 404, the tubular braided element is returned to a compressed configuration at the tip of the catheter channel. This is optionally made by pulling the tubular braided element further in the channel and then pushing the distal end of the tubular braided element in a distal direction, bringing the distal end thereof toward the tip of the catheter channel. Now, as shown at 405, the tubular braided element may be re-expanded to treat another target area in the blood vessel.

It is expected that during the life of a patent maturing from this application many relevant passive and active in vivo materials will be developed and the scope of the terms braided, braided-head, tube, wire, catheter, and sheath are intended to include all such new technologies a priori.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An ablation catheter system comprising:
    a channel;
    a tubular braided element having an outer circumferential surface and a lumen, said tubular braided element being sized and shaped to be enclosed inside said channel when in a compressed configuration and to be expanded in a target area of a target blood vessel in an expanded configuration, wherein in said expanded configuration said outer circumferential surface is adapted to a contour and a varied width of said target area of said target blood vessel, and touches walls of said target blood vessel in said target area along a longitudinal dimension of said tubular braided element to apply a substantially uniform wounding force to the walls of said target blood vessel along said longitudinal dimension; and
    a longitudinal maneuvering element which is mechanically connected to a distal end of said tubular braided element and set to pull said distal end into said lumen so as to curve radially and outwardly a plurality of annular segments of said expanded tubular braided element around an imaginary torus in a sequential manner such that a wounding force different than said substantially uniform wounding force is applied to said walls of said target blood vessel.

2. The system of claim 1, wherein said channel is an inner channel which is placed in and along a catheter, said inner channel allows placing said tubular braided element in place while retracting said inner channel, facilitating said tubular braided element to expand from said compressed configuration to said expanded configuration.

3. The system of claim 1, wherein said blood vessel is a vein.

4. The system of claim 1, wherein said tubular braided element comprises a mesh having a plurality of parallel fibers each with a different rigidity coefficient.

5. The system of claim 1, wherein at least said outer circumferential surface is coated with a drug.

6. The system of claim 1, further including a fluid channel located within said channel and set to conduct fluid along said channel, between said target area and an extrabody container.

7. The system of claim 6, wherein said fluid channel has a fluid releasing head at an end proximal to said target area, said fluid releasing head having at least one aperture directed to release fluid toward said walls or to withdraw fluid from said target area.

8. The system of claim 1, wherein said tubular braided element is made from a fiber made of a material selected from a group consisting of: metallic fiber, organic fiber, glass fiber, bio-reactive fiber, catalytic fiber, bio-soluble fiber, inert fiber, highly flexible fiber, abrasive fiber, single filament fiber, and a combination of the aforesaid.

9. The system of claim 1, wherein said braided element is adapted to be partially expanded in said target area in a manner that a portion of said braided element remains enclosed inside said channel and another portion of said braided element expands outside said channel such that an outer circumferential surface of said another portion is adapted to said contour and said varied width of said target area of said blood vessel, and touches the walls of said target blood vessel in said target area along said longitudinal dimension of said tubular braided element to apply said substantially uniform wounding force to the walls of said target blood vessel along said longitudinal dimension.

10. A method for treating a blood vessel, comprising:
conducting a tubular braided element having an outer circumferential surface and a lumen in a compressed configuration using a catheter channel to a target area in a target blood vessel;
extracting at least a portion of said tubular braided element from said channel so as to expand said portion in a manner that said outer circumferential surface applies a first pressure on walls of said target area of said target blood vessel, wherein a distal end of said tubular braided element is inversely folded into said lumen;
pulling said distal end of said tubular braided element into said lumen so as to curve radially and outwardly a plurality of annular segments of said at least a portion of said tubular braided element in a sequential manner;
further pulling said tubular braided element in said channel further after said distal end exceeds said lumen in a proximal direction;
pushing said tubular braided element to bring said distal end to a proximity with a tip of said channel; and
conducting said tubular braided element to another target area in said blood vessel;
wherein each said annular segment applies a second pressure on said walls of said target area of said target blood vessel when being curved, said second pressure being higher than said first pressure.

11. The method of claim 10, wherein said pulling comprises wounding said walls of said target area of said target blood vessel during said pulling.

12. The method of claim 10, wherein each said annular segment is curved in a poloidal direction.

13. The method of claim 10, further comprising conducting a drug along said channel and releasing said drug during said pulling.

14. The method of claim 10, wherein said extracting is performed by maintaining an orientation of said tubular braided element along said target area while retracting said channel.

15. The method of claim 10, further comprising repeating the steps of extracting, pulling, and further pulling in said another target area.

* * * * *